US010052125B2

(12) United States Patent
Rosenthal et al.

(10) Patent No.: US 10,052,125 B2
(45) Date of Patent: Aug. 21, 2018

(54) ATHERECTOMY CATHETER WITH LATERALLY-DISPLACEABLE TIP

(71) Applicant: AVINGER, INC., Redwood City, CA (US)

(72) Inventors: Michael H. Rosenthal, Menlo Park, CA (US); Michael Zung, San Carlos, CA (US); Nicholas J. Spinelli, San Carlos, CA (US); Charles W. McNall, Cottonwood Heights, UT (US); John B. Simpson, Woodside, CA (US); John F. Black, San Mateo, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

(21) Appl. No.: 15/354,898

(22) Filed: Nov. 17, 2016

(65) Prior Publication Data

US 2017/0065293 A1    Mar. 9, 2017

Related U.S. Application Data

(63) Continuation of application No. 12/829,277, filed on Jul. 1, 2010, now Pat. No. 9,498,600.
(Continued)

(51) Int. Cl.
*A61B 17/3207*    (2006.01)
*A61M 25/00*      (2006.01)
(Continued)

(52) U.S. Cl.
CPC .............. *A61B 17/320758* (2013.01); *A61B 17/32075* (2013.01); *A61B 90/361* (2016.02);
(Continued)

(58) Field of Classification Search
None
See application file for complete search history.

(56) References Cited

U.S. PATENT DOCUMENTS 3,908,637 A    9/1975  Doroshow
4,178,935 A   12/1979  Gekhaman et al.
(Continued)

FOREIGN PATENT DOCUMENTS

CN    1875242 A    12/2006
CN    1947652 A     4/2007
(Continued)

OTHER PUBLICATIONS

Aziz et al.; Chronic total occlusions—a stiff challege requiring a major breakthrough: is there light at the end of the tunnel?; Heart; vol. 91; suppl. III; pp. 42-48; Jun. 2005.
(Continued)

*Primary Examiner* — Katherine Fernandez
(74) *Attorney, Agent, or Firm* — Shay Glenn LLP

(57) ABSTRACT

Described herein are atherectomy catheters, systems and methods that include a distal tip region that may be moved laterally so that its long axis is parallel with the long axis of the main catheter body axis. Displacing the distal tip region laterally out of the main catheter body axis exposes an annular blade and opens a passageway for cut tissue to enter a storage region within the catheter. The annular blade may be internally coupled to a drive shaft that rotates the blade, and thus the exposed blade edge may have the same crossing profile (OD) as the rest of the distal end region of the catheter. Also described herein are gear-driven atherectomy devices that may use a cable drive shaft to actuate the annular blade. Both push-to-cut and pull-to-cut variations are described, as are methods for cutting tissue and systems including these atherectomy catheters.

26 Claims, 16 Drawing Sheets

Related U.S. Application Data

(60) Provisional application No. 61/222,242, filed on Jul. 1, 2009.

(51) Int. Cl.
  *A61M 25/01* (2006.01)
  *A61B 90/00* (2016.01)
  *A61B 17/29* (2006.01)
  *A61B 17/32* (2006.01)

(52) U.S. Cl.
  CPC .... *A61M 25/0074* (2013.01); *A61M 25/0133* (2013.01); *A61B 2017/2927* (2013.01); *A61B 2017/320064* (2013.01); *A61B 2017/320766* (2013.01); *A61B 2017/320791* (2013.01); *A61B 2090/3614* (2016.02)

(56) References Cited

U.S. PATENT DOCUMENTS

| | | | |
|---|---|---|---|
| 4,527,553 | A | 7/1985 | Upsher |
| 4,552,554 | A | 11/1985 | Gould et al. |
| 4,621,353 | A | 11/1986 | Hazel et al. |
| 4,639,091 | A | 1/1987 | Huignard et al. |
| 4,654,024 | A | 3/1987 | Crittenden et al. |
| 4,686,982 | A | 8/1987 | Nash |
| 4,771,774 | A | 9/1988 | Simpson et al. |
| 4,841,977 | A | 6/1989 | Griffith et al. |
| 4,857,046 | A | 8/1989 | Stevens et al. |
| 4,926,858 | A | 5/1990 | Gifford, III et al. |
| 5,000,185 | A | 3/1991 | Yock |
| 5,041,082 | A | 8/1991 | Shiber |
| 5,047,040 | A | 9/1991 | Simpson et al. |
| 5,085,662 | A | 2/1992 | Willard |
| 5,099,850 | A | 3/1992 | Matsui et al. |
| 5,178,153 | A | 1/1993 | Einzig |
| 5,182,291 | A | 1/1993 | Gubin et al. |
| 5,190,050 | A | 3/1993 | Nitzsche |
| 5,192,291 | A | 3/1993 | Pannek, Jr. |
| 5,312,415 | A | 5/1994 | Palermo |
| 5,312,425 | A | 5/1994 | Evans et al. |
| 5,321,501 | A | 6/1994 | Swanson et al. |
| 5,333,142 | A | 7/1994 | Scheps |
| 5,358,472 | A | 10/1994 | Vance et al. |
| 5,366,464 | A | 11/1994 | Belknap |
| 5,383,460 | A | 1/1995 | Jang et al. |
| 5,383,467 | A | 1/1995 | Auer et al. |
| 5,429,136 | A | 7/1995 | Milo et al. |
| 5,431,673 | A * | 7/1995 | Summers ....... A61B 17/320758 606/167 |
| 5,459,570 | A | 10/1995 | Swanson et al. |
| 5,460,168 | A | 10/1995 | Masubuchi et al. |
| 5,465,147 | A | 11/1995 | Swanson |
| 5,507,795 | A | 4/1996 | Chiang et al. |
| 5,556,405 | A | 9/1996 | Lary |
| 5,620,426 | A | 4/1997 | Braithwaite |
| 5,632,754 | A | 5/1997 | Farley et al. |
| 5,632,755 | A | 5/1997 | Nordgren et al. |
| 5,674,232 | A | 10/1997 | Halliburton |
| 5,681,336 | A | 10/1997 | Clement et al. |
| 5,690,634 | A | 11/1997 | Muller et al. |
| 5,722,403 | A | 3/1998 | McGee et al. |
| 5,795,295 | A | 8/1998 | Hellmuth et al. |
| 5,807,339 | A | 9/1998 | Bostrom et al. |
| 5,830,145 | A | 11/1998 | Tenhoff |
| 5,836,957 | A | 11/1998 | Schulz et al. |
| 5,843,050 | A | 12/1998 | Jones et al. |
| 5,843,103 | A | 12/1998 | Wulfman |
| 5,868,778 | A | 2/1999 | Gershony et al. |
| 5,872,879 | A | 2/1999 | Hamm |
| 5,904,651 | A | 5/1999 | Swanson et al. |
| 5,907,425 | A | 5/1999 | Dickensheets et al. |
| 5,935,075 | A | 8/1999 | Casscells et al. |
| 5,938,602 | A | 8/1999 | Lloyd |
| 5,951,482 | A | 9/1999 | Winston et al. |
| 5,951,581 | A | 9/1999 | Saadat et al. |
| 5,951,583 | A | 9/1999 | Jensen et al. |
| 5,956,355 | A | 9/1999 | Swanson et al. |
| 5,957,952 | A | 9/1999 | Gershony et al. |
| 5,987,995 | A | 11/1999 | Sawatari et al. |
| 5,997,558 | A | 12/1999 | Nash |
| 6,001,112 | A | 12/1999 | Taylor |
| 6,007,530 | A | 12/1999 | Dornhofer et al. |
| 6,010,449 | A | 1/2000 | Selmon et al. |
| 6,013,072 | A | 1/2000 | Winston et al. |
| 6,017,359 | A | 1/2000 | Gershony et al. |
| 6,027,514 | A | 2/2000 | Stine et al. |
| 6,032,673 | A | 3/2000 | Savage et al. |
| 6,048,349 | A | 4/2000 | Winston et al. |
| 6,080,170 | A | 6/2000 | Nash et al. |
| 6,106,515 | A | 8/2000 | Winston et al. |
| 6,110,164 | A | 8/2000 | Vidlund |
| 6,120,515 | A | 9/2000 | Rogers et al. |
| 6,120,516 | A | 9/2000 | Selmon et al. |
| 6,134,002 | A | 10/2000 | Stimson et al. |
| 6,134,003 | A | 10/2000 | Tearney et al. |
| 6,152,938 | A | 11/2000 | Curry |
| 6,152,951 | A | 11/2000 | Hashimoto et al. |
| 6,160,826 | A | 12/2000 | Swanson et al. |
| 6,175,669 | B1 | 1/2001 | Colston et al. |
| 6,176,871 | B1 | 1/2001 | Pathak et al. |
| 6,183,432 | B1 * | 2/2001 | Milo ............... A61B 17/22012 604/22 |
| 6,193,676 | B1 | 2/2001 | Winston et al. |
| 6,206,898 | B1 | 3/2001 | Honeycutt et al. |
| 6,228,076 | B1 | 5/2001 | Winston et al. |
| 6,241,744 | B1 | 6/2001 | Imran et al. |
| 6,283,957 | B1 | 9/2001 | Hashimoto et al. |
| 6,290,668 | B1 | 9/2001 | Gregory et al. |
| 6,294,775 | B1 | 9/2001 | Seibel et al. |
| 6,299,622 | B1 | 10/2001 | Snow et al. |
| 6,307,985 | B1 | 10/2001 | Murakami et al. |
| 6,402,719 | B1 | 6/2002 | Ponzi et al. |
| 6,416,527 | B1 | 7/2002 | Berg et al. |
| 6,445,939 | B1 | 9/2002 | Swanson et al. |
| 6,445,944 | B1 | 9/2002 | Ostrovsky |
| 6,447,525 | B2 | 9/2002 | Follmer et al. |
| 6,451,036 | B1 | 9/2002 | Heitzmann et al. |
| 6,454,717 | B1 | 9/2002 | Pantages et al. |
| 6,454,779 | B1 | 9/2002 | Taylor |
| 6,482,216 | B1 | 11/2002 | Hiblar et al. |
| 6,482,217 | B1 | 11/2002 | Pintor et al. |
| 6,485,413 | B1 | 11/2002 | Boppart et al. |
| 6,497,649 | B2 | 12/2002 | Parker et al. |
| 6,501,551 | B1 | 12/2002 | Tearney et al. |
| 6,503,261 | B1 | 1/2003 | Bruneau et al. |
| 6,511,458 | B2 | 1/2003 | Milo et al. |
| 6,517,528 | B1 | 2/2003 | Pantages et al. |
| 6,542,665 | B2 | 4/2003 | Reed et al. |
| 6,546,272 | B1 | 4/2003 | MacKinnon et al. |
| 6,551,302 | B1 | 4/2003 | Rosinko et al. |
| 6,563,105 | B2 | 5/2003 | Seibel et al. |
| 6,564,087 | B1 | 5/2003 | Pitris et al. |
| 6,565,588 | B1 | 5/2003 | Clement et al. |
| 6,572,563 | B2 | 6/2003 | Ouchi et al. |
| 6,572,643 | B1 | 6/2003 | Gharibadeh |
| 6,575,995 | B1 | 6/2003 | Huter et al. |
| 6,579,298 | B1 | 6/2003 | Bruneau et al. |
| 6,615,071 | B1 | 9/2003 | Casscells, III et al. |
| 6,638,233 | B2 | 10/2003 | Corvi et al. |
| 6,645,217 | B1 | 11/2003 | MacKinnon et al. |
| 6,657,727 | B1 | 12/2003 | Izatt et al. |
| 6,666,874 | B2 | 12/2003 | Heitzmann et al. |
| 6,687,010 | B1 | 2/2004 | Horii |
| 6,728,571 | B1 | 4/2004 | Barbato |
| D489,973 | S | 5/2004 | Root et al. |
| 6,730,063 | B2 | 5/2004 | Delaney et al. |
| 6,758,854 | B1 | 7/2004 | Butler et al. |
| 6,760,112 | B2 | 7/2004 | Reed et al. |
| 6,800,085 | B2 | 10/2004 | Selmon et al. |
| 6,818,001 | B2 | 11/2004 | Wulfman et al. |
| 6,824,550 | B1 | 11/2004 | Noriega et al. |
| 6,830,577 | B2 | 12/2004 | Nash et al. |
| 6,845,190 | B1 | 1/2005 | Smithwick et al. |

(56) References Cited

U.S. PATENT DOCUMENTS

| | | |
|---|---|---|
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,498,247 B2 | 11/2016 | Patel et al. |
| 9,498,600 B2 | 11/2016 | Rosenthal et al. |
| 9,557,156 B2 | 1/2017 | Kankaria |
| 2001/0020126 A1 | 9/2001 | Swanson et al. |
| 2002/0019644 A1* | 2/2002 | Hastings ............. A61B 17/22 606/159 |
| 2002/0038097 A1* | 3/2002 | Corvi ............. A61B 10/0275 600/564 |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0158547 A1 | 10/2002 | Wood |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1* | 8/2004 | Simpson ........ A61B 17/320758 606/159 |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |

(56) References Cited

U.S. PATENT DOCUMENTS

| | | |
|---|---|---|
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038173 A1 | 2/2007 | Simpson |
| 2007/0078469 A1 | 4/2007 | Soito et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1* | 3/2008 | Olson ............ A61B 17/320758 606/159 |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1* | 11/2009 | Bielewicz ................ A61B 8/12 600/424 |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0080016 A1 | 4/2010 | Fukui et al. |
| 2010/0125253 A1 | 5/2010 | Olson et al. |
| 2010/0130996 A1 | 5/2010 | Doud et al. |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Miao et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0257478 A1 | 10/2011 | Kleiner et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0004506 A1 | 1/2012 | Tearney et al. |
| 2012/0238869 A1 | 9/2012 | Schmitt et al. |
| 2013/0096589 A1 | 4/2013 | Spencer et al. |
| 2013/0138128 A1 | 5/2013 | Patel et al. |
| 2013/0289392 A1 | 10/2013 | Patel et al. |
| 2013/0296695 A1 | 11/2013 | Spencer et al. |
| 2014/0005534 A1 | 1/2014 | He et al. |
| 2014/0213893 A1 | 7/2014 | Simpson et al. |
| 2015/0141816 A1 | 5/2015 | Gupta et al. |
| 2015/0208922 A1 | 7/2015 | Simpson et al. |
| 2015/0272615 A1 | 10/2015 | Newhauser et al. |
| 2015/0320975 A1 | 11/2015 | Simpson et al. |
| 2016/0008025 A1 | 1/2016 | Gupta et al. |
| 2016/0029902 A1 | 2/2016 | Smith et al. |
| 2016/0038030 A1 | 2/2016 | Smith et al. |
| 2016/0135832 A1 | 5/2016 | Simpson et al. |
| 2016/0144155 A1 | 5/2016 | Simpson et al. |
| 2016/0192962 A1 | 7/2016 | Simpson et al. |
| 2016/0262791 A1 | 9/2016 | Patel et al. |
| 2016/0262839 A1 | 9/2016 | Spencer et al. |
| 2016/0338582 A1 | 11/2016 | Tachibana et al. |
| 2017/0238803 A1 | 8/2017 | Kankaria |
| 2017/0238808 A1 | 8/2017 | Simpson et al. |

FOREIGN PATENT DOCUMENTS

| | | |
|---|---|---|
| CN | 101601581 A | 12/2009 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | 03502060 A | 2/1990 |
| JP | 05103763 A | 4/1993 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005-533533 A | 11/2005 |
| JP | 2008-175698 A | 7/2006 |
| JP | 2006-288775 A | 10/2006 |

(56) References Cited

FOREIGN PATENT DOCUMENTS

| | | |
|---|---|---|
| JP | 2006-313158 A | 11/2006 |
| JP | 2006-526790 | 11/2006 |
| JP | 2006-326157 A | 12/2006 |
| JP | 2007-83053 A | 4/2007 |
| JP | 2007-83057 A | 4/2007 |
| JP | 2007-225349 A | 9/2007 |
| JP | 2007533361 A | 11/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-66252 A | 4/2009 |
| JP | 2009-78150 A | 4/2009 |
| JP | 2010042182 A | 2/2010 |
| JP | 2010518900 A | 6/2010 |
| JP | 2011521747 A | 7/2011 |
| JP | 2012533353 A | 12/2012 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO01/15609 A1 | 3/2001 |
| WO | WO 01/76680 A1 | 10/2001 |
| WO | WO 2006/133030 A2 | 12/2006 |
| WO | WO2008/005888 A2 | 1/2008 |
| WO | WO 2008/029506 A1 | 3/2008 |
| WO | WO 2008/042987 A2 | 4/2008 |
| WO | WO2008/051951 A1 | 5/2008 |
| WO | WO2008/065600 A2 | 6/2008 |
| WO | WO 2008/086613 A1 | 7/2008 |
| WO | WO 2008/087613 A2 | 7/2008 |
| WO | WO2009/005779 A1 | 1/2009 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A1 | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |

OTHER PUBLICATIONS

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Linares et al.; Arbitrary single-mode coupling by tapered and nontapered grin fiber lenses; Applied Optics; vol. 29; No. 28; pp. 4003-4007; Oct. 1, 1990.

Sharma et al.; Optical coherence tomography based on an all-fiber autocorrelator using probe-end reflection as reference; CWJ13; San Francisco, California; CLEO May 16, 2004; 4 pages.

Suparno et al.; Light scattering with single-mode fiber collimators; Applied Optics; vol. 33; No. 30; pp. 7200-7205; Oct. 20, 1994.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Patel et al.; U.S. Appl. No. 15/354,842 entitled "Atherectomy catheters and occlusion crossing devices," filed Nov. 17, 2016.

Patel et al.; U.S. Appl. No. 15/324,325 entitled "High speed chronic total occulusion crossing devices," filed Jan. 6, 2017.

Simpson et al.; U.S. Appl. No. 15/457,960 entitled "Atherectomy catheters devices having multi-channel bushings," filed Mar. 13, 2017.

Patel et al.; U.S. Appl. No. 15/480,238 entitled "Guidewire positioning catheter," filed Apr. 5, 2017.

* cited by examiner

  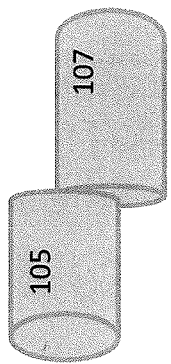   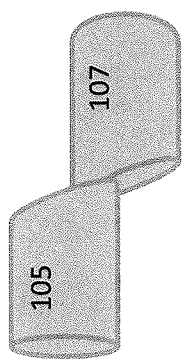
  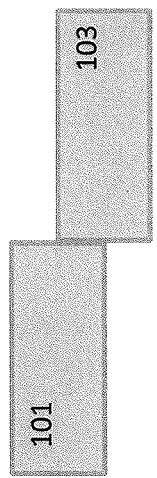   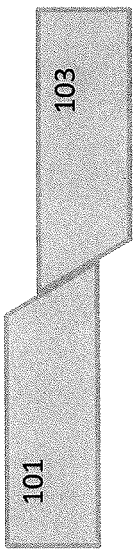

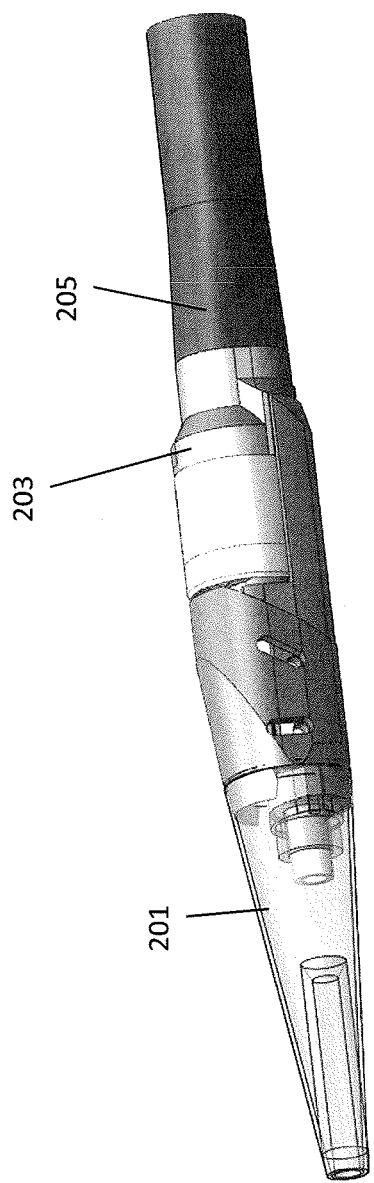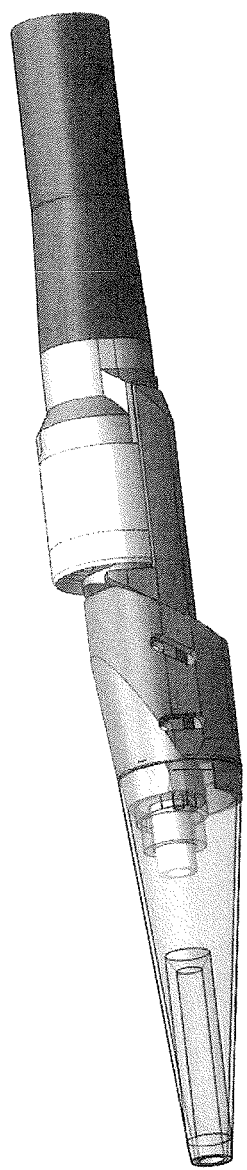
FIG. 2A
FIG. 2B

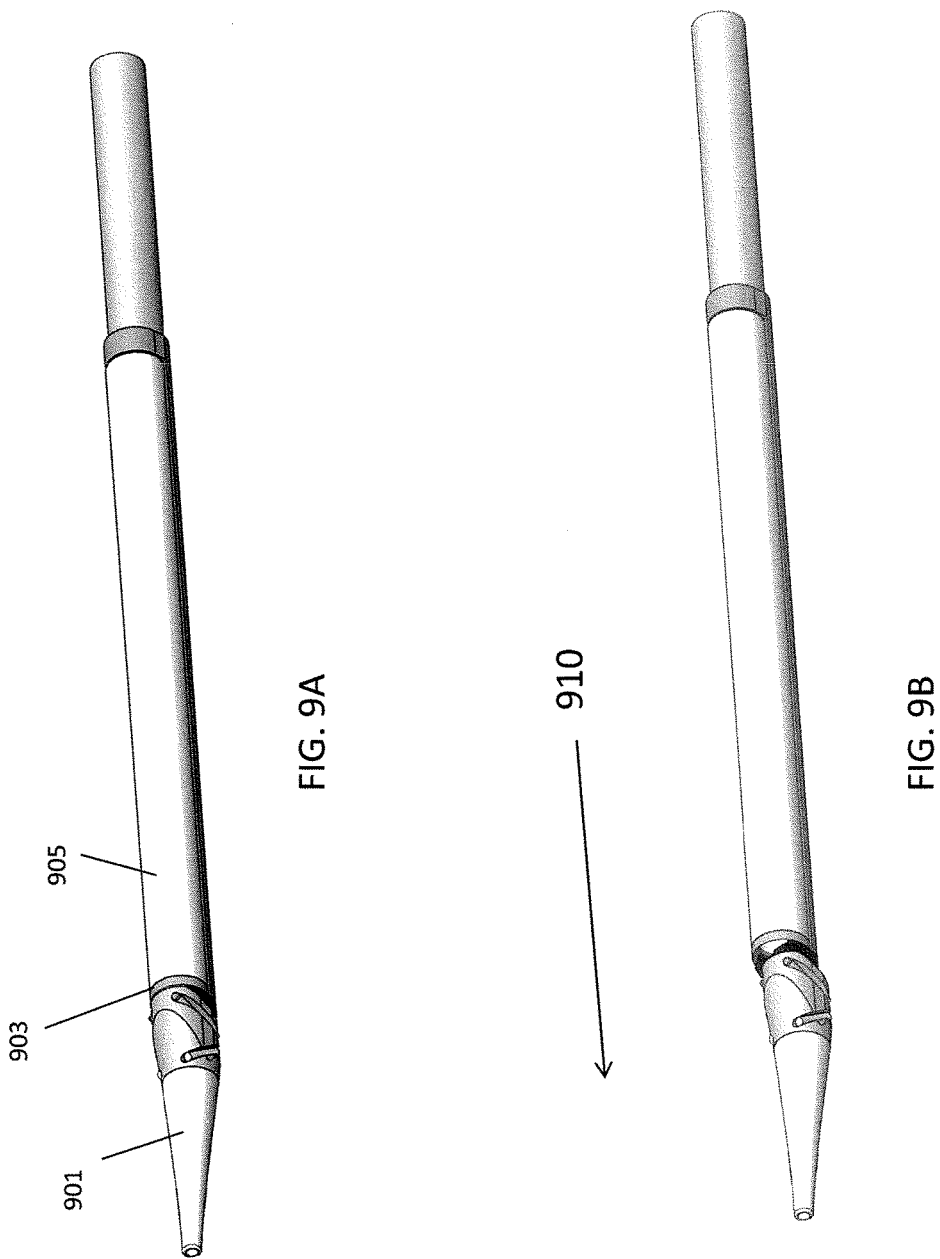

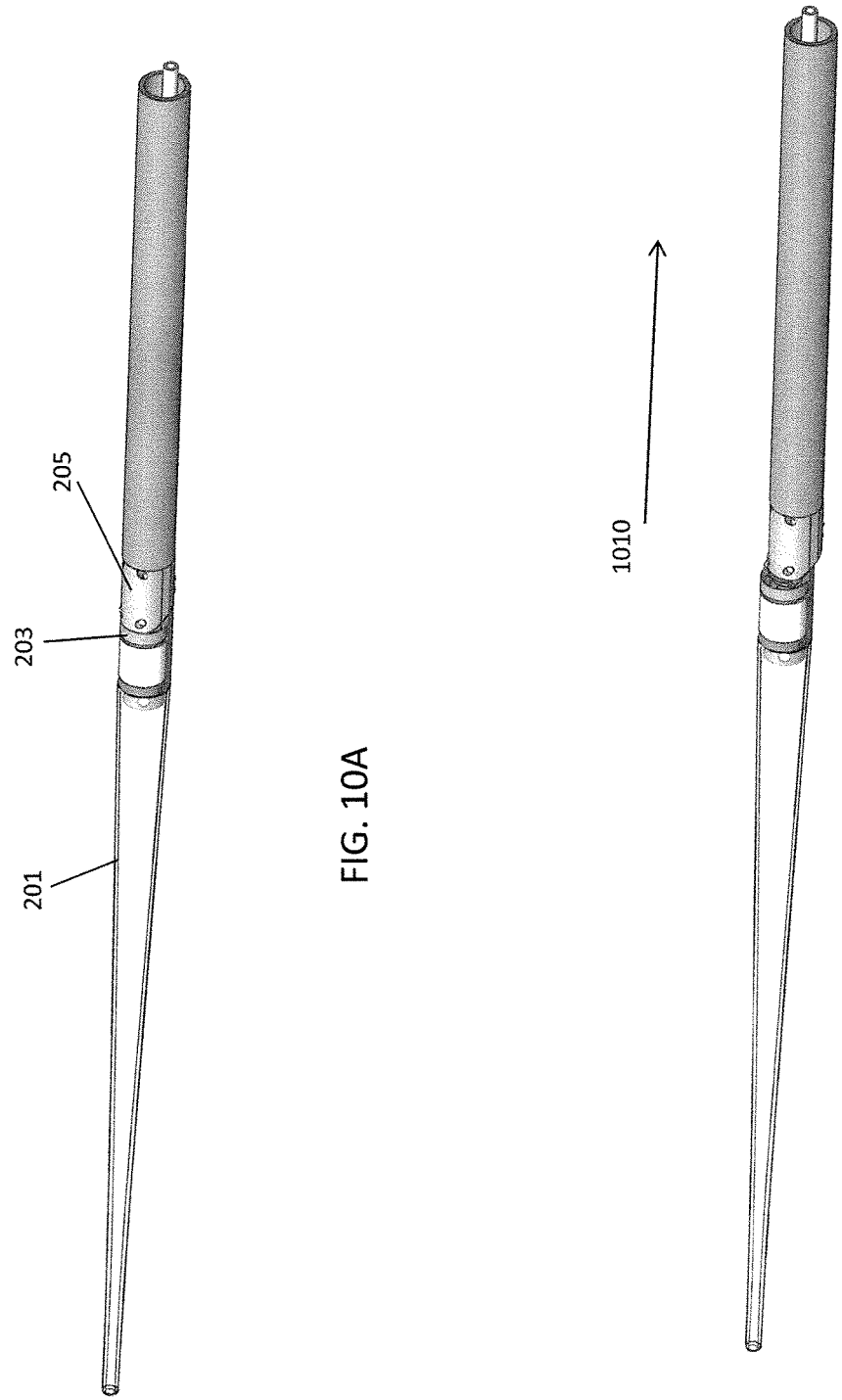

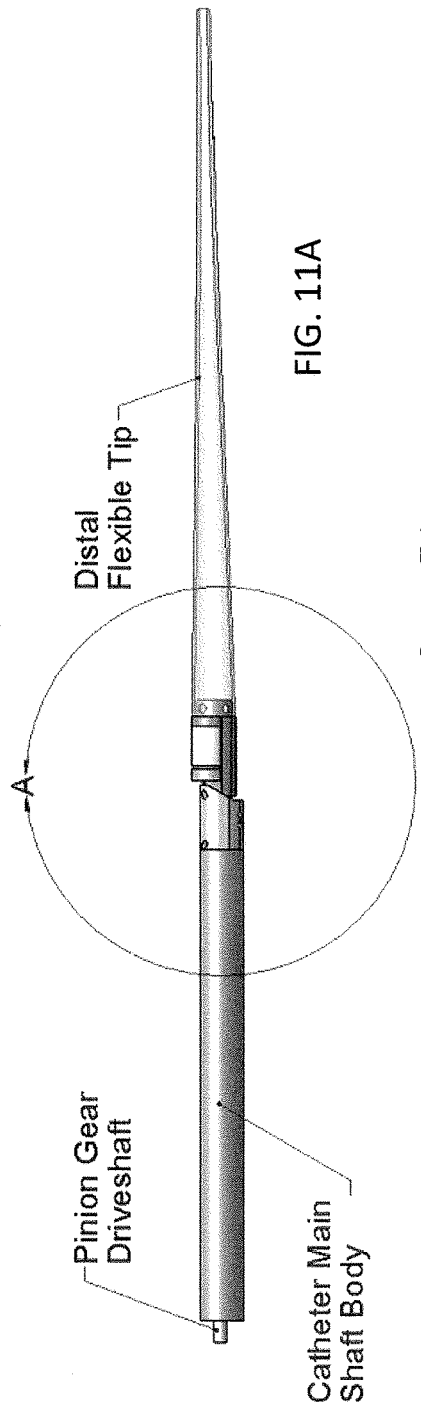
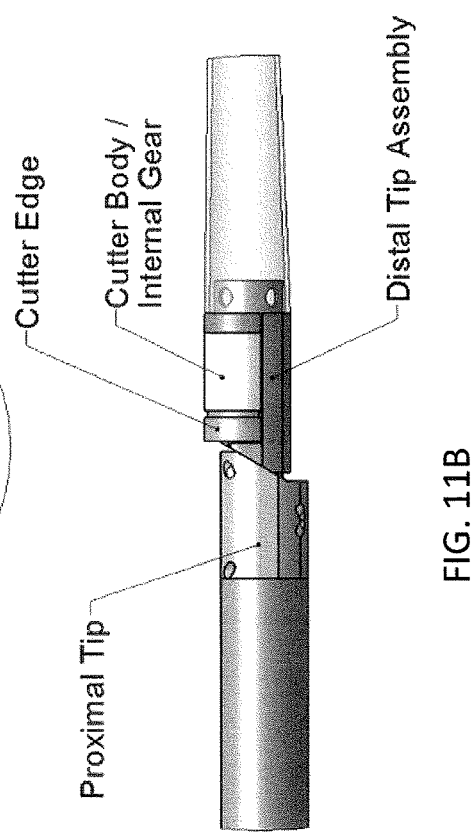
FIG. 11A
FIG. 11B

ATHERECTOMY CATHETER WITH LATERALLY-DISPLACEABLE TIP

CROSS REFERENCE TO RELATED APPLICATIONS

This patent application is a continuation of U.S. patent application Ser. No. 12/829,277, filed Jul. 1, 2010, titled "ATHERECTOMY CATHETER WITH LATERALLY-DISPLACEABLE TIP," now U.S. Pat. No. 9,498,600, which claims priority to U.S. Provisional Patent Application No. 61/222,242, titled "GEAR DRIVEN ATHERECTOMY CATHETER" filed on Jul. 1, 2009.

This application may also be related to U.S. patent application Ser. No. 12/790,703, titled "OPTICAL COHERENCE TOMOGRAPHY FOR BIOLOGICAL IMAGING," filed on May 28, 2010.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

Described herein are atherectomy catheters with laterally displaceable tips, systems including such catheters and methods of using them.

BACKGROUND OF THE INVENTION

A significant body of scientific and clinical evidence supports atherectomy as a viable primary or adjunctive therapy prior to stenting for the treatment of occlusive coronary artery disease. Atherectomy offers a simple mechanical advantage over alternative therapies. By removing the majority of plaque mass (debulking) it creates a larger initial lumen and dramatically increases the compliance of the arterial wall. As a result, stent deployment is greatly enhanced.

Additionally, there are advantages related to the arterial healing response. When circumferential radial forces are applied to the vasculature, as in the case of angioplasty or stenting, the plaque mass is displaced, forcing the vessel wall to stretch dramatically. This stretch injury is a known stimulus for the cellular in-growth that leads to restenosis. By removing the disease with minimal force applied to the vessel and reducing the plaque burden prior to stent placement, large gains in lumen size can be created with decreased vessel wall injury and limited elastic recoil which have shown to translate into better acute results and lower restenosis rates.

Traditional atherectomy devices have been plagued by a number of problems, which have severely limited market adoption. These challenges include the need for large access devices, rigid distal assemblies that make control and introduction challenging, fixed cut length, unpredictable depth of cut, insufficient tissue collection and removal, and complex operation. The systems and devices described herein may overcome these hurdles and offer physicians a safe, reliable, and simple cutting system that offers the precision required in eccentric lesions, various disease states, and tortuous anatomy.

Despite the potential to improve restenosis rates associated with angioplasty and stenting in the coronary and peripheral vasculature, atherectomy is not commonly performed. The primary reason for this limited use is the cost, complexity and limited applicability of currently available devices. Many designs are unable to treat the wide range of disease states present in long complex lesions; luminal gain is often limited by the requirement of the physician to introduce multiple devices with increased crossing profiles; tissue collection is either unpredictable or considered unnecessary based on assumptions regarding small particle size and volumes; and optimal debulking is either not possible due to lack of intravascular visualization or requires very long procedure times. Based on these limitations current devices are likely to perform poorly in the coronary vasculature where safety and efficacy in de novo lesions, ostials, and bifurcations continue to pose great challenges.

Previously, atherectomy devices focused on macerating or emulsifying the atherosclerotic plaque such that it may be considered clinically insignificant and remain in the blood stream or aspirated proximally through small spaces in the catheter main body. The reliability of these devices to produce clinically insignificant embolization has been questioned when not aspirated through the catheter to an external reservoir. Aspiration requires a vacuum be applied to a lumen or annular space within the catheter to remove emulsified tissue. In early clinical evaluations of aspiration the presence of negative pressure at the distal working assembly cause the artery to collapse around the cutting element causing more aggressive treatment, dissections and/or perforations. In addition, the option for post procedural analysis of any removed disease is extremely limited or impossible. Atheromed, Pathway Medical and Cardio Vascular Systems, Inc. are examples of companies working on such product designs.

Other atherectomy devices include the directional atherectomy devices such as those developed by DVI and FoxHollow. These catheters use cupped cutters that cut and "turn" the tissue distal into a storage reservoir in the distal tip of the device. This approach preserves the "as cut" nature of the plaque but requires large distal collection elements. These large distal tip assemblies can limit the capabilities of the system to access small lesions and create additional trauma to the vessel.

Currently available atherectomy devices also do not include, and are poorly adapted for use with, real time image guidance. Physician practice is often to treat target lesion as if they contain concentric disease even though intravascular diagnostic devices have consistently shown significantly eccentric lesions. This circumferential treatment approach virtually ensures that native arterial wall and potentially healthy vessel will be cut from the vasculature.

Atherectomy catheter devices, systems and methods that may address some of these concerns are described and illustrated below.

SUMMARY OF THE INVENTION

Described herein are atherectomy catheters, systems including them and methods of using them. Some of the distinguishing features that may be included as part of these devices, systems and methods are summarized below.

In general the atherectomy devices described herein include laterally displaceable distal tip regions. Lateral displacement of the distal tip region typically means that the longitudinal axis of the distal tip region is radially displaced relative to the longitudinal axis of the distal end of the rest of the catheter body. Longitudinal displacement of the distal tip region effectively drops the distal tip region away from the rest of the catheter body, and may expose one or more cutting regions on or in the catheter, and provide an opening into which cut tissue may enter for storage and/or removal.

In some variations, the catheters described herein include an annular cutting ring or element having at least one cutting edge. An annular cutting ring may be a cylindrical element (or a partial cylinder) that has at least one sharpened or cutting edge. The sharp/cutting edge may be sharp, tapered, serrated, or otherwise configured to cut into tissues such as those within a diseased lumen of a vessel. The annular cutting edge may be rotatable, typically rotating about a long axis that is parallel to the direction of cutting (i.e., the longitudinal axis of the catheter). The cutting edge of the annular cutting ring may be located along one edge, such as the circular lip of a cylindrical-shaped annular cutting ring.

In some variations, the annular cutting ring includes one or more outwardly-facing non-cutting sides. The outwardly-facing side(s) of the annular cutting ring may form an external surface of the catheter. In some variations the annular cutting ring is approximately the width of the catheter, which may maximize the size of the cutting edge of the annular cutting ring.

Any of the devices described herein may be gear-driven, and may include a gear driven distal assembly that may provide additional flexibility for locating a cutter driving element at or near the distal end of the catheter. Annular cutting rings that are driven by a geared driveshaft may offer mechanical advantages compared to annular cutters driven by a rotating driveshaft that is concentric to, and housed within, the main body of the catheter shaft. Driveshafts that are directly coupled to the cutter blade may be driven with standard DC motors, hydraulics or pneumatics. However, the concentric configuration may limit the space proximal to the cutting element available for proximal tissue storage and/or removal. The catheter described herein may include both gear-driven and directly-coupled driveshaft embodiments.

The mechanical advantage provided by the geared cutting assemblies described herein also provides additional design options for the cutting mechanisms. This approach would require lower input torque and driveshaft performance requirements necessary to power a cutter through very hard calcified lesions. Different gear ratios may be used in designs intended to cut soft tissue or hard disease. It is also possible for multiple gear ratios to be provided in one device to be modified by the physician as deemed necessary.

Any of the atherectomy catheters described herein may also be used to cut and store tissue for later analysis and/or for removal from the body. For example, the devices described herein may include a primary hollow cutter and internal gear driven configuration that may allow tissue to travel directly through the cutter, from distal to proximal, once planed from the arterial wall and be stored proximal to the cutter in its "as cut" state, allowing for future histological evaluations. In some variations, the gearing means and direction of distal tip motion when activating the cutter may ensure appropriate position of apposition force for the cutter to engage tissue.

The laterally displaceable distal tip regions may help ensure close longitudinal proximity of the cutting edge (e.g., a proximal tip edge) or tissue shearing edge, to the wall of the vessel and reliably link the amount of cutter exposure to the depth of cut independent of the amount of cutter apposition force.

The laterally displaceable distal tip assembly may be displaceable directly downward, preserving parallel alignment of the tip and catheter shaft axis, and providing efficient use of energy sources for simplified device actuation and manipulation. The lateral displacement may also allow intravascular imaging elements located on the distal assembly of the device to provide real time diagnostic information to physician.

Guided atherectomy systems are described herein. These devices are intended to access the vasculature using conventional catheterization techniques employing sheath and/or guiding catheter access and tracking over a positioned pre-positioned guidewire. The atherectomy devices described herein may be adapted for use with a guidewire or sheath. For example, the atherectomy catheter may include a central guidewire lumen. The catheters described herein may generally track through the vasculature to the target lesion.

In some variations, the devices include visualization, and particularly Optical Coherence Tomography (OCT) image visualization. For example, in some variations, a fiber affixed or positioned at or near the distal assembly of the device and extending proximally will enable OCT imaging to be used for lesion assessment and treatment planning. In use, the device may be rotationally oriented toward the diseased sector of the artery, and the device may be activated using proximal physician controls so that the distal tip assembly will laterally displace (e.g., moving away from the cutter) to expose the cutting edge to the diseased tissue. The annular cutter may be rotated, e.g., at approximately 100 to 10000 rpm. The device may then be translated through the lesion to plane and cut the diseased tissue while the OCT image provides real time feedback regarding wall and disease characteristics, cutter apposition and cut depth. During a cutting pass, the tissue may feed into the catheter and travel through the hollow cutter and into a proximal tissue reservoir. Upon completing the cutting pass, the proximal controls may be used to deactivate the device, closing the tip against the spinning cutter and terminating the planed tissue with a scissoring action and stopping cutter rotation. Multiple runs through this procedure may occur to fully treat the disease.

Atherectomy catheters and systems using them may have a cutter (e.g., the cutting edge of an annular cutting ring) diameter at or near the maximum crossing profile of the main catheter body, which may maximize cut tissue cross-sectional area, and minimize the depth of cut. The large cross-sectional area may reduce the procedure time, providing more efficient cutting passes and add a degree of safety by reducing the depth of cut required to achieve these efficiencies. The depth of the cut may be controlled by the lateral displacement of the distal end of the device, which both determines the opening size and how much of the cutter is exposed, and may also drive the cutter against the wall of the vessel by effectively widening the device within the vessel lumen.

The hollow cutters (annular cutting rings) described may allow tissue to be cut from the wall of the artery, pass directly through the catheter, and be stored in a reservoir. Both forward-cutting (push-cutting devices) and reverse (pull) cutting devices are described. In pull-cutting devices, the tissue may preferentially be stored distally, which in push cutting devices, the tissue may be preferentially be stored proximally. In some variations a deflector or guide may be used to direct the cut tissue into a proximal and/or distal storage area within the device. Proximal tissue storage may allow the distal tip region diameters and lengths to be reduced. Reduced tip dimensions may help the device cross tight lesions, cut in quickly tapering vessels, and generally be less traumatic to downstream vascular structures.

In variations including an internal gear driven cutter, the annular cutting ring may include female gears on the cutter body internal diameter. This may provide a large, mainly centralized, region for tissue to pass through the cutter and into a proximal storage area, as mentioned. The gear mechanism may also provide a mechanical advantage to the cutting assembly. In the embodiments described below, the input torque applied to the input pinion drive shaft may be 0.5× of that required by a direct drive system to cut hard/calcified disease. The driveshaft may balance flexibility to navigate tortuous anatomy and torsional/tensile/compressive rigidity to drive distal mechanisms through hard calcium or tight lesions. The mechanical advantage of the internal gear drive may provide more options for driveshaft design. In addition, an internal gear may help achieve better engagement of micro scale tooth profiles. Fabrication of gears of this scale can be challenging, and the increased tooth engagement of the internal gear configuration may limit wear of the materials and increase tooth engagement leading to longer life and more consistent torque output and shock absorption.

The tissue entry window is mainly defined by the vertical distance from outer tip diameter to cutter edge, which may minimize longitudinal motion and reduce angular deflection of the tip mechanism. As mentioned, the depth of the cut may remain relatively constant at varied force of engagement between cutter and tissue because of the lateral displacement of the distal tip region.

As mentioned, any of the variations described herein may include on-board imaging with one or more imaging elements providing a cross-sectional view of vessel wall morphology in the cutting plane. For example, ultrasound and/or optical imaging technologies may be used. In particular, OCT imaging may be used. In some variations, the OCT imaging system may achieve around 10 micron lateral resolution and use optical fibers having diameters below 0.010".

In some variations of the cutter assemblies described herein, the annular cutting ring and the laterally displaceable distal tip allow consistent cut depths even with high apposition forces. Angiography and intravascular imaging technologies may be used and a known depth of cut may be overlaid on known depth of disease. Typically, the apposition force applied may directly correlate to the vessel diameter and to the level of stenosis, reducing the potential for barotrauma and over treatment.

In some variations, the catheter device also includes a handle having one or more controls for controlling the catheter. For example, the system or device may include a handle having a control for laterally displacing the distal tip region and exposing the cutting edge of the annular cutting ring. Any appropriate control may be used, including a button, switch, slider, knob, etc. The lateral displacement may be controlled by a mechanical, electrical, and/or magnetic means. For example, an elongate tendon member (e.g., wire) which may be flexible may extend through the catheter body from proximal to distal ends to actuate the lateral displacement.

In addition, the devices or systems may also include one or more controls for controlling the rotation of the annular cutting ring. Rotation may be linked to the lateral displacement so that the cutter begins rotating either shortly before or after lateral displacement exposes the cutter. Alternatively, the rotation may be independent of the lateral displacement. The devices or systems may also include controls for an associate imaging (e.g., OCT) system. In some variations the device or system includes control logic for regulating the displacement and/or rotation and/or imaging. Proximal controls may include an automated advancement function to ensure proximal motion correlates to distal tracking in the vessel. In some variations, some or all of these controls may be on a handle, or may be on a separate controller.

Force limiting controls may also be used to ensure the input forces do not exceed what is required to effectively cut diseased tissue. This may reduce the chances of the device moving outside the perimeter of the lesion while activated thereby cutting into healthy arterial wall.

In some variations, the catheter systems described herein are compatible with 7F sheath access to the peripheral arteries, or 6F sheath sizes.

For example, described herein are atherectomy catheters for cutting tissue having a laterally displaceable tip. These devices may include: an elongate, flexible catheter body having a proximal end and a distal end and a longitudinal axis; an elongate and laterally displaceable distal tip assembly; a rotatable annular cutting ring between the distal end of the catheter body and the distal tip assembly; and a distal tip control at the proximal end of the catheter that is configured to expose a cutting edge of the annular cutting ring by laterally displacing the distal tip assembly from a closed configuration in which the distal tip assembly is in-line with the catheter body, to an open configuration in which the distal tip assembly is laterally displaced from the catheter body and parallel to the longitudinal axis of the catheter body.

Any of these devices may also include a drive shaft extending along the length of the catheter body. For example, the drive shaft may comprise a cable drive shaft having a distal gear configured to drive rotation of the cutting ring. In some variations, the annular cutting ring comprises internal gear teeth configured to mate with a drive shaft to rotate the cutting ring.

The drive shaft may be directly connected to the annular cutting ring. For example, the drive shaft comprises a hollow tubular drive shaft.

Any of the catheters described herein may include a guidewire lumen extending the length of the catheter. The lumen may be centered or off-centered, and one or more additional lumens may also be included.

In some variations, the annular cutting ring may form an outer surface of the catheter in both the closed and open configurations.

The device may also include an internal tissue collection region configured to receive tissue cut by the annular cutting ring. For example, the tissue collection region may be located within the distal tip assembly. The tissue collection region may be located within the catheter body.

In some variations, the annular cutting ring may be displaceable with the distal tip assembly. For example "pull to cut" embodiments, in which the tissue is cut as the catheter is withdrawn proximally, may include the annular cutting ring on the displaceable distal tip. In some variations the annular cutting ring remains in-line with the catheter body when the distal tip assembly is displaced.

As mentioned, in any of these variations, the catheter may include an OCT imaging subassembly. For example, the OCT imaging subassembly may include a fiber optic extending the length of the catheter body. The OCT imaging assembly may comprise a side-facing OCT emitting element fixed proximal to the annular cutting ring.

The OCT imaging assembly may include a side-facing OCT emitting element fixed distally to the annular cutting ring.

Also described herein are atherectomy catheters for cutting tissue having a laterally displaceable tip. These devices may include: an elongate catheter body having a longitudinal axis; a laterally displaceable distal tip assembly; an annular cutting ring between the catheter body and the distal tip assembly; and a distal tip control configured to switch the distal tip assembly between a closed configuration, in which the distal tip assembly is in-line with the catheter body, and an open configuration exposing a cutting edge of the annular cutting ring, in which the distal tip assembly is laterally displaced from the catheter body and parallel to the longitudinal axis of the catheter body.

Also described herein are atherectomy catheters for cutting tissue having a laterally displaceable tip, the devices having: an elongate, flexible catheter body having a proximal end and a distal end and a longitudinal axis; an elongate and laterally displaceable distal tip assembly; an annular cutting ring between the distal end of the catheter body and the distal tip assembly forming an outer surface of the atherectomy catheter; and a distal tip control at the proximal end of the catheter that is configured to switch the distal tip assembly from a closed configuration in which the distal tip assembly is in-line with the catheter body, and an open configuration in which the distal tip assembly is laterally displaced from the catheter body and parallel to the longitudinal axis of the catheter body, exposing a cutting edge of the annular cutting ring.

Also described herein are atherectomy catheters for cutting tissue having a laterally displaceable tip, including: an elongate catheter body having a longitudinal axis; a laterally displaceable distal tip assembly; an annular cutting ring between the catheter body and the distal tip assembly, wherein the cutting ring includes an internal gear surface; a drive shaft extending the length of the catheter body having a driving pinion gear for driving rotation of the annular cutting ring; and a distal tip control configured to switch the distal tip assembly between a closed configuration, in which the distal tip assembly is in-line with the catheter body, and an open configuration exposing a cutting edge of the annular cutting ring, in which the distal tip assembly is laterally displaced from the catheter body and parallel to the longitudinal axis of the catheter body.

The driving pinion gear and the internal gear surface of the annular cutting ring may be configured to provide a mechanical advantage for turning the annular cutting ring. The devices may also include a guidewire lumen extending the length of the catheter. In some variations, the annular cutting ring forms an outer surface of the catheter in both the closed and open configurations.

Also described herein are methods of performing an atherectomy to remove tissue from within a vessel lumen using an atherectomy catheter having a catheter body with a longitudinal axis, an annular cutting ring and a laterally displaceable distal tip assembly, the method comprising: advancing the atherectomy catheter within a vessel lumen; exposing a cutting edge of the annular cutting ring of the atherectomy catheter by laterally displacing the distal tip assembly away from the longitudinal axis of the catheter body so that the distal tip assembly is parallel to the longitudinal axis of the catheter body; and driving the cutting edge against a wall of the vessel lumen to remove tissue.

Any of these methods may also include the step of rotating the annular cutting ring while driving it against the wall of the vessel lumen. The annular ring may be rotated by driving an internal gear within an inner surface of the annular ring. The method may also include the step of imaging the tissue using an OCT imaging subassembly on the catheter.

The driving step may comprise pushing the catheter distally, and/or pulling the catheter proximally. Any of these methods may also include the step of collecting cut tissue within an opening of the atherectomy catheter.

Also described herein are methods of performing an atherectomy to remove tissue from within a vessel lumen using an atherectomy catheter having a catheter body, annular cutting ring and a laterally displaceable distal tip assembly, the method may include the steps of: advancing the atherectomy catheter within a vessel lumen while the distal tip assembly is in-line with the catheter body of the atherectomy catheter so that the distal tip assembly and the catheter body have a common longitudinal axis; laterally displacing the distal tip assembly to expose a cutting edge of the annular cutting ring so that the longitudinal axis of the distal tip assembly is parallel but laterally offset from the longitudinal axis of the catheter body; and driving the cutting edge against a wall of the vessel lumen while rotating the annular ring to remove tissue.

The annular ring may be rotated by driving an internal gear within an inner surface of the annular ring.

In some variations, the method further include the step of imaging the tissue using an OCT imaging subassembly on the catheter. In any of the methods described herein, the step of driving the catheter may include pushing the catheter distally and/or pulling the catheter proximally. Any of these methods may also include the step of collecting cut tissue within an opening of the atherectomy catheter.

BRIEF DESCRIPTION OF THE DRAWINGS

FIG. 1A-1H illustrates different examples of lateral displacement.

FIG. 2A is an isometric view of a catheter having a laterally displaceable distal tip region in a closed/non-activated configuration.

FIG. 2B is an isometric view of the catheter of FIG. 2A showing the distal tip region laterally displaced.

FIG. 9A is an isometric view of another variation of an atherectomy catheter having a laterally displaceable distal tip region in a closed/non-activated configuration.

FIG. 9B is an isometric view of the catheter of FIG. 9A showing the distal tip region laterally displaced.

FIG. 10A is an isometric view of another variation of an atherectomy catheter having a laterally displaceable distal tip region in a closed/non-activated configuration.

FIG. 10B is an isometric view of the catheter of FIG. 10A showing the distal tip region laterally displaced.

FIGS. 11A and 11B show annotated side perspective views of a catheter such as the one shown in FIGS. 10A-10D.

DETAILED DESCRIPTION OF THE INVENTION

Figure 2C:
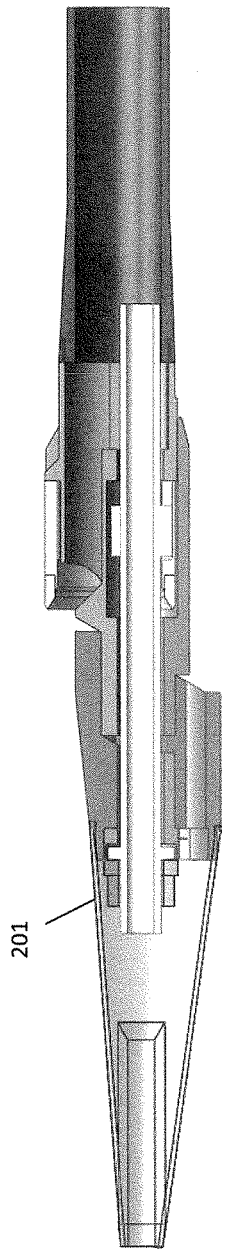
FIG. 2C is a cross-sectional view of the catheter shown in FIG. 2B, above (in the open/laterally displaced configuration).

In general the atherectomy devices described herein include laterally displaceable distal tip regions. FIG. 1A-1H illustrate examples of lateral displacement. As used herein, lateral displacement includes movement of the distal tip region of a catheter from a first position in which the long axis of the distal tip region (the longitudinal axis of the distal tip region) is in-line with the long axis of the proximal body of the catheter (the longitudinal axis of the catheter body) to a second, laterally displaced, position in which the distal tip region has shifted out plane so that the long axis of the distal tip region is parallel with the long axis of the catheter body, but in a different plane. The terms "parallel" and "in line" in reference to the long or longitudinal axis do not require that the catheter regions be straight.

FIGS. 1A and 1B, illustrate lateral displacement of a rectangular region having a proximal 101 and distal 103 elements. In FIG. 1A, the proximal 101 and the distal 103 regions are in-line, and share a common longitudinal (long) axis, which may be imagined as a horizontal axis that passes through the midline of both rectangular regions. In FIG. 1B, the distal 103 element has been laterally displaced relative to the proximal 101 element, and has shifted upwards. Although the longitudinal axis of the proximal 101 element and the longitudinal axis of the distal 103 element are still approximately parallel, they are no longer in-line, but have separated by a radial distance.

FIGS. 1C and 1D illustrate another example, in which the proximal 101 and distal 103 rectangular elements are laterally and slightly longitudinally displaced. Similar examples of lateral displacement are illustrated for cylindrical shapes in FIGS. 1E to 1H. FIGS. 1E and 1F show lateral displacement of a proximal 105 and distal 107 elements along a plane perpendicular to the long axis. FIGS. 1G and 1H illustrate lateral displacement of proximal 105 and distal 107 cylindrical elements along a non-perpendicular plane that (similar to FIGS. 1C and 1D) also result in a slight longitudinal displacement.

FIGS. 2A-8B illustrate one variations of an atherectomy catheter device having a laterally displaceable distal tip region. These variations are configured as gear-driven catheters, in which the cutter is an annular cutting ring that includes a sharp or cutting edge along one side, and includes internal threads on the inner surface of the ring.

For example, FIG. 2A shows a distal portion of a device in a "non-activated" configuration, in which the distal tip region 201 is in-line with the catheter body 205 (or at least the region of the catheter body adjacent to the distal tip region). FIG. 2B shows the same catheter in an "activated" configuration. In the closed/non-activated position, the cutter 203 is protected and is not exposed, which may prevent unintended damage to the inner diameter of ancillary medical devices and the vasculature. In the open/activated position, the distal tip assembly 201 is laterally displaced to expose up to 180 degrees of the cutter edge. When opened, the bottom circumference of the tip assembly increases the overall crossing profile (e.g., diameter) of the device. This enlarged configuration (the distance between bottom tip surface and upper cutter edge) may extend the inner lumen of the vessel (e.g., artery) and create an opposing force for cutter engagement into the tissue. This appositional force may ensure the purchase of the cutting edge against the targeted cutting site will be enough to both engage the tissue and maintain contact during the cutting pass.

Figure 2D:
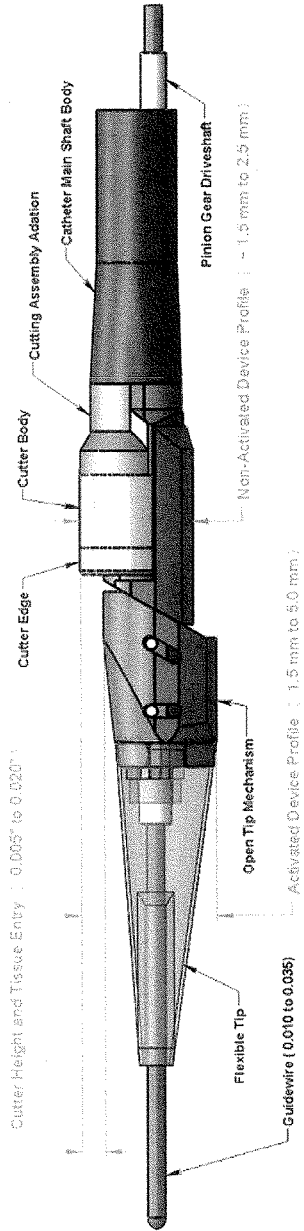
FIG. 2D is a side view of the catheter shown in FIG. 2B.
Figure 3A:
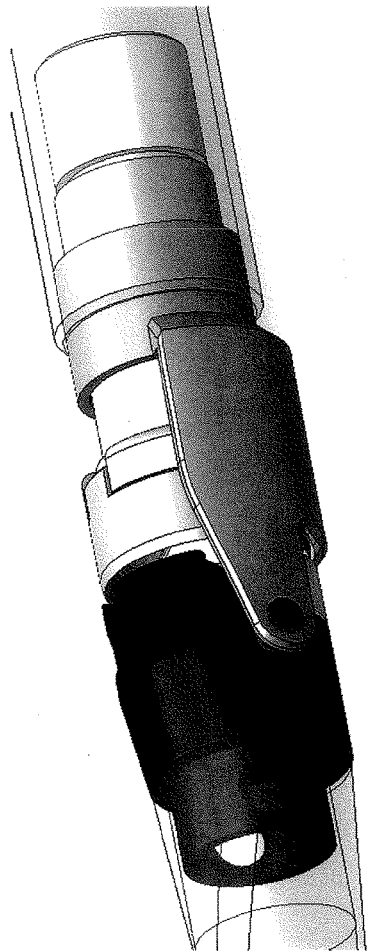
FIGS. 3A and 3B illustrate one variation of an actuation mechanism (which may be referred to as a "collar actuation method") for opening (laterally displacing) and closing the distal tip assembly.
Figure 3B:
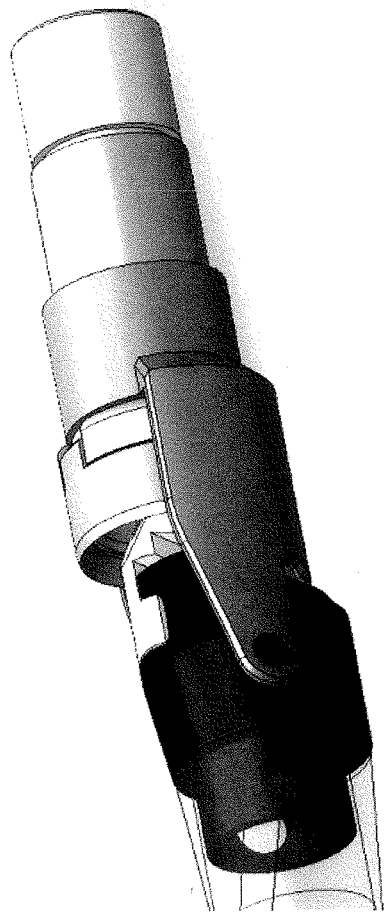

The tip actuation method shown in FIGS. 2A and 2B involves sliding a pinion gear drive shaft relative to the cutter assembly. FIG. 2C is a cross-sectional view of the distal assembly of FIGS. 2A-2B. FIG. 2D is an annotated side view of the same device. As illustrated in these figures, as the pinion driveshaft is forced forward in the assembly 201, the proximal 60 degree mating faces and pin slots of the cutting assembly adaptation and tip mechanism may force the tip forward (distal) and down. The angle and distance traveled by the tip may be modified with different face angles and relative pin slot positions. Similar tip actuation methods may be accomplished by translating a collar proximal to the cutter assembly that is attached via a pin and slot design. Translation of this collar will actuate the assembly. An example of this may be shown in FIGS. 3A and 3B.

As illustrated herein, the distal tip assembly or apposition element may be laterally displaced and "drop" directly downward in plane with the main body of the catheter. This y-axis coincidence provides at least two benefits: (1) deflection and/or a curved portion of the distal device assembly may cause rotational instability in tortuous vasculature as the device travels the path of least resistance (curve or deflection continued alignment with bend/turn in the vessel); and (2) cutter apposition forces with a deflected tip configuration that may be applied up and downstream of the cutting location, and may be defined by vascular characteristics potentially a long distance from the key target. This direct "downward" activation of the tip assembly ensures that an apposition force is applied local to the cutting assembly. Apposition force near directly 180 degrees of the cutter edge may make certain that the target lesion define the amount of engagement between cutter and tissue.

In addition, laterally displacing the distal tip assembly and/or cutter exposure with minimal longitudinal motion and no angular deflection of the tip mechanism may provide for the tissue entry window to be mainly defined by the vertical distance from outer tip diameter to cutter edge. This may prevent increased tissue invagination into the exposed tissue entry point with increased apposition forces. Depth of cut may then remain relatively constant at varied force of engagement between cutter and tissue providing the physician with a more predictable and safe device.

Alternate methods of tip actuation may include using a worm gear anchored to a pinion gear driveshaft and rack anchored to the tip assembly. Rotation of the pinion gear drive shaft to rotate the cutter may additionally advance and displace the tip. The direction of rotation may be alternated to open and close the system. Alternatively, a balloon and/or inflatable lumen may be placed between the tip mechanism and cutting assembly adaptation such that inflation will push the tip mechanism off axis. Magnetic elements may also be used to actuate the assembly by taking advantage of the natural means of attraction or repulsion or by preferentially applying an electrical current. Finally, as discussed below and represented in FIG. 6, helical gears may be used for the cutter body internal gears and pinion gear such that the pitch angle may be altered to provide an axial actuation force vector when driving the cutter. In some variations, the distal tip assembly/region may be actuated by a push/pull tendon that extends the length of the catheter.

In some variations, the apposition force for cutter engagement may be achieved by means of a balloon mounted on the circumference of the catheter distal assembly, approximately 180 degrees from the cutting plane. The inflation of this balloon would also increase the effective size of the device, distend the artery, and engage the cutter into the tissue. A highly lubricious base balloon material and/or hydrophilic coating may be used such that the balloon may be in contact with the wall of the artery during the cutting traverse. The balloon may be made of an elastic or inelastic material.

A "sponge" like material may also be used to preferentially appose the cutter in the same manner as the inflated balloon or lumen discussed above. Exposing the porous and absorbent material to infused fluid or blood would expand the material and actuate the tip or directly apply force to the wall of the artery. By extracting the fluid with negative pressure or mechanical compression the overall dimensions of the absorber would be reduced to deactivate the system.

In the catheter variation shown in FIGS. 2C and 2D, the axis of the guide wire Lumen and Pinion Drive Shaft are aligned in both open and closed positions of the distal tip assembly. This may ensure minimal sliding friction as the device is advanced and retracted over the wire. In some variations it may be advantageous to have the guidewire lumen crimp or bend on the guidewire.

Figure 4A:
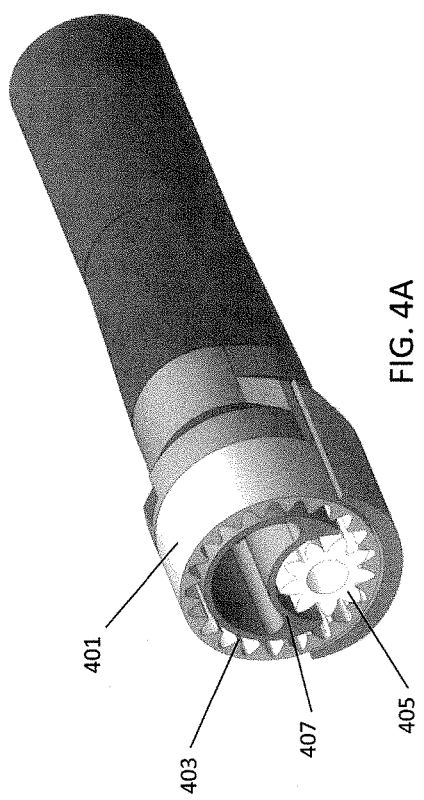
FIGS. 4A and 4B show isometric and face views of an off-axis driving pinion gear and internal gear surface of the cutter body.
Figure 4B:
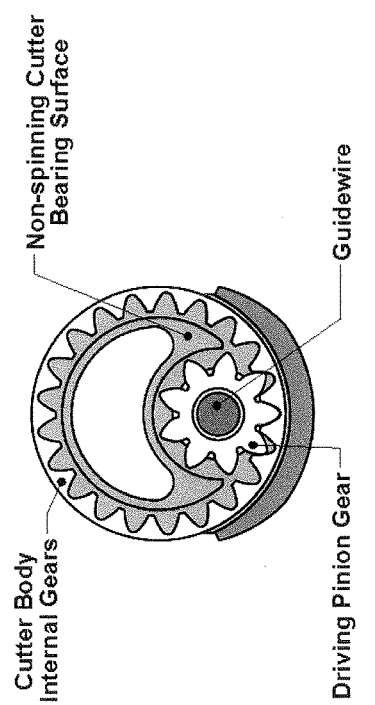

FIGS. 4A and 4B illustrate one variation of a primary internal gear assembly with an approximate 2 to 1 gear ratio between internal cutter body and pinion. The annular cutting ring 401 includes internal gear teeth ("female" teeth) 403 on the inner surface that is configured to mate with the driving pinion gear 405. The means for controlling the offset of the internal and pinion gear axis is the supporting non-spinning cutter bearing surface 407. This component may be manufactured from a high grade engineering plastic or high wear coefficient material. The annular "bean" shaped inner lumen may thus define a lumen or space for cut tissue to be stored or to travel through in the catheter. This support component also isolates the gear teeth from the tissue specimen. This component may also ensure an appropriate engagement force is maintained according to gear tooth profile requirements.

Figure 5:
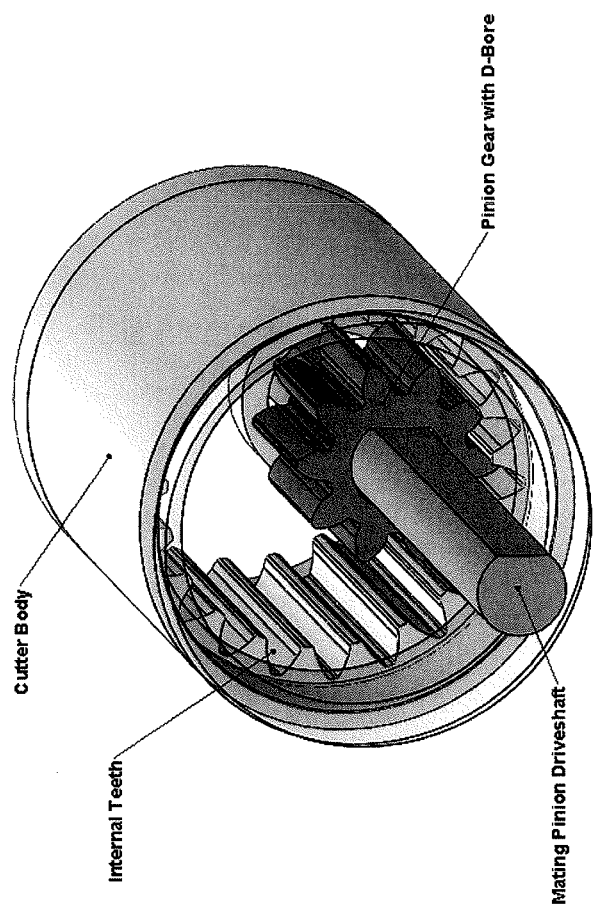
FIG. 5 illustrates a perspective view of a gear-driven annular cutting ring including internal gears and a D-bore pinion gear configuration.
Figure 6:
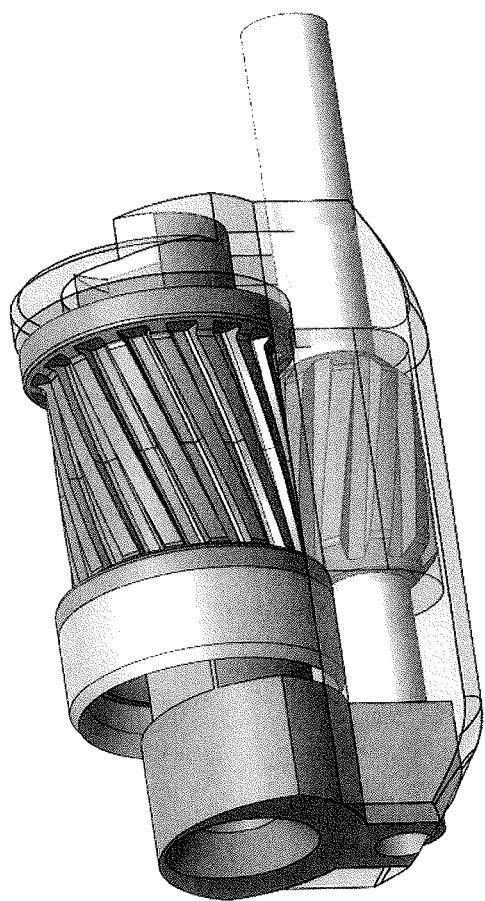
FIG. 6 shows one example of a helical gear.

As mentioned, in some variations, the pinion driveshaft translation may used to actuate the tip. This pinion gear driveshaft may be anchored longitudinally to the pinion gear, as shown in FIG. 2D, or it may be free to translate relative to the pinion, as shown in FIG. 5. In the case where the driveshaft slides relative to the pinion, an asymmetric mating x-section of the driveshaft and pinion gear may be present to ensure proper torque transmission between components. In this example, the pinion gear may not be required to slide relative to the cutter body while spinning.

As discussed above, a helical gear configuration may be used for the cutter driving assembly. A left-hand pitch angle on the cutter body, and mating pinion pitch would provide proximal thrust with clockwise rotation of the pinion. Relative longitudinal motion created by axial thrust can be used to actuate the distal tip. In addition, this proximal force will seat the cutter within the mating assembly to ensure the cutting edge is predictably aligned with distal window defining and shearing edges. Finally, the helical configuration may provide more gear tooth surface area engagement per length of assembly at each angular position to ensure small gears have more opportunity to transmit the required torque.

Figure 7:
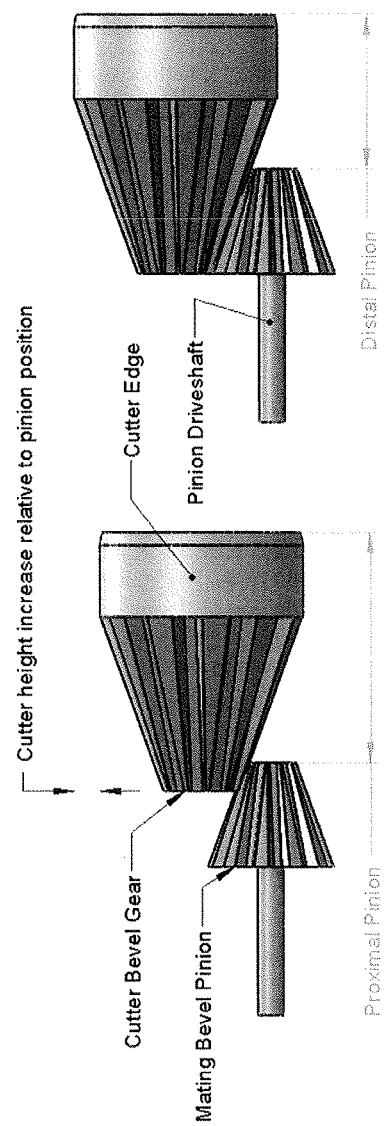
FIG. 7 illustrates, in principle, a bevel gear drive and cutter exposure

A bevel gear interaction may also be used to drive the cutter assembly. As shown in FIG. 7, a pinion bevel gear and driveshaft may remain concentric to a fixed catheter axis and may translate along that axis. In some variations, the moving bevel pinion may be dome-shaped so that the grooves/teeth engage fully. A bevel gear and cutter edge assembly may be fixed longitudinally relative to a main catheter body but be free to move perpendicular to the mating bevel pinion axis. Translation of the pinion gear along its axis of rotation may change the position of the cutter relative to the catheter axis and consequently raise or lower the cutter to expose the cutting edge.

In any of these variations, the catheter device may also include on-board and real time image guidance capabilities. This may include an imaging element, or energy emitting assembly, positioned at the distal portion of the device such that local images of the vessel may guide device usage. One specific configuration of an OCT system that may be used for this distal imaging element is described in co-pending applications, including U.S. patent application Ser. No. 12/790,703, previously incorporated by reference. The distal energy emitter(s) may be positioned in multiple locations in fixed positions or embodied in a mating assembly that may translate in an eccentric lumen or in the hollow lumen of the driveshaft. The emitter may send and receive relevant light or sound signals at 90 degrees from the catheter axis or at angles up to approximately 50 degrees to visualize distal or proximal wall features from a fixed position.

Figure 8:
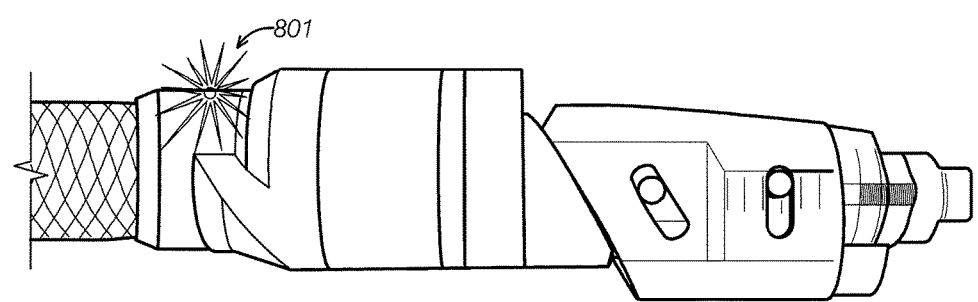
FIG. 8 shows one example of a catheter having a laterally displaceable distal tip assembly and an OCT imaging fiber.

FIG. 8 shows one example of a catheter having a laterally displaceable distal tip assembly and an OCT imaging fiber. The imaging fiber is configured for placement of the OCT sensing element 801 (the end of the fiber forming the "window") just proximal to cutter body and positioned such that images are obtained in the cutting direction. The OCT sensing element 801 is a side-facing element. In this example, the OCT window is fixed in position on the side, and angular survey mages of the adjacent vessel region may be taken by rotating the entire catheter around the vessel and/or moving it longitudinally as well. This image scanning may preferably be done before laterally displacing the distal tip assembly. In some variation the sensor (window) is positioned in more distal locations, including in the displaceable distal tip, which may allow visualization of the region ahead of tissue removal in push removal devices.

The emitting element may be positioned distal and/or proximal to the cutter edge. Distal placement would provide information during a cutting pass prior to the cutter interacting with the tissue and, therefore, allow the physician to stop or continue cutting as disease changes in depth and/or position. Proximal placement would also provide guidance regarding cut quality, depth and cutting efficiency. FIG. 9 shows an example of the energy emitting portion of the fiber optic assembly mounted proximal to the cutter edge and fixed on the cutting side of the catheter main body.

Furthermore, the data collected at the distal end of the catheter, after transmitted and appropriately processed, may drive an automated means of tip actuation and cutter position. Increased amounts of disease detected by the software may automatically increase tip axially offset consequently increasing cut depth and apposition force. Cutter speeds, gear ratios and torque inputs may be adjusted according to input from the imaging system.

Figure 9C:
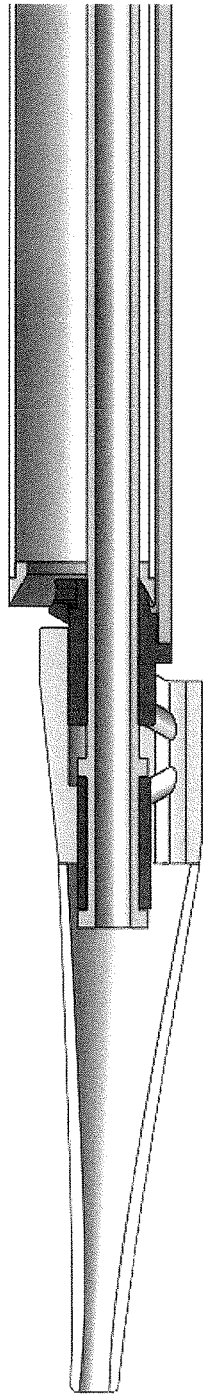
FIG. 9C is a cross-sectional view of the catheter shown in FIG. 9B in the open/laterally displaced configuration.

FIGS. 9A-9D illustrate another variation of an atherectomy catheter having a laterally displaceable distal tip assembly as described herein. In this example, the annular cutting ring 903 is also positioned between the distal tip assembly 901 and the rest of the catheter body 905. The annular cutting ring also forms a portion of the outer surface of the catheter, although the cutting edge is protected or "closed" by the distal tip assembly as shown in FIG. 9A. In this embodiment, the annular cutting ring is directly coupled to the drive shaft, which is not geared. The drive shaft may be a braided or solid tube which is bonded at the distal end to the annular cutting ring.

In FIGS. 9A and 9B, the distal portion of the catheter device is shown in the non-activated and activated positions, respectively. This embodiment is in many ways similar to the variations discussed above. In the closed/non-activated position the cutter is protected to prevent unintended damage to the inner diameter of ancillary medical devices and vasculature. In the open/activated position the tip assembly is dropped to expose up to half of the cutter edge. When open, the bottom circumference of the tip assembly increases the overall crossing profile of the device. This maximum dimension between bottom tip surface and upper cutter edge extends to the inner lumen of the artery and creates an opposing force for cutter engagement into the tissue. This appositional force may help ensure the position of the cutting edge against the targeted cutting site will both engage the tissue and maintain contact during the cutting pass.

The tip actuation method shown in FIGS. 9A-9D involves sliding the tip actuation mechanism relative to the cutter assembly. As the mechanism is advanced distally in the assembly, the proximal angled mating faces and pin slots of the cutting assembly adaptation and tip mechanism force the tip forward (distal) and down. The angle and distance traveled by the tip may be modified with different face angles and relative pin slot positions.

As before, the distal tip assembly thus laterally displaces (dropping directly downward in the figure), in parallel with the main body of the catheter.

Figure 9D:
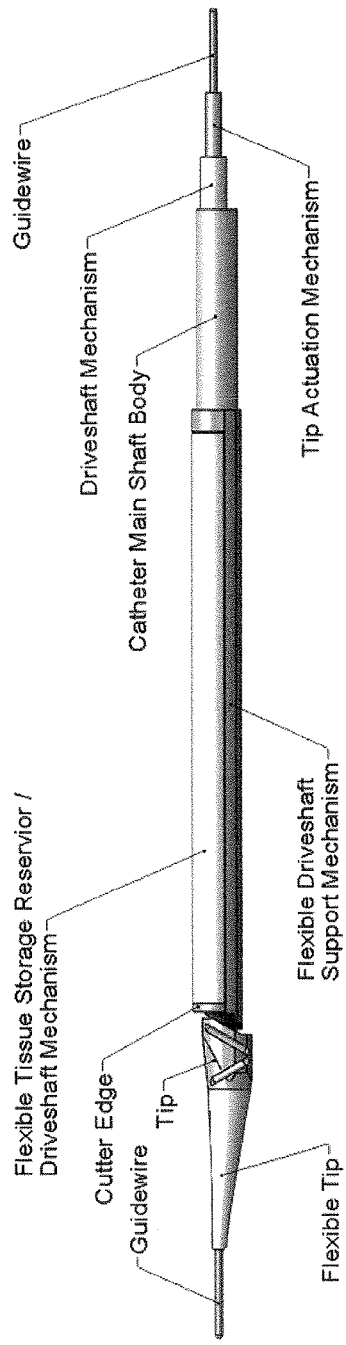
FIG. 9D is a side perspective view of the catheter shown in FIG. 9B.

FIG. 9C shows a cross-section through the device of FIG. 9B (shown with the laterally displaced distal tip assembly), and FIG. 9D is a labeled and annotated side perspective view. In this example, the catheter body contains the driveshaft mechanism, and also forms a proximal tissue storage region which may be positioned within the drive shaft.

FIGS. 10A-13 illustrate another variation of an atherectomy catheter with a laterally displaceable distal tip region. In this example, the atherectomy device is configured as a pull-cutter, so that the tissue may be cut by positioning the device within the vessel, laterally displacing the distal tip assembly, and pulling the catheter proximally to cut tissue from within the vessel.

Figure 10C:
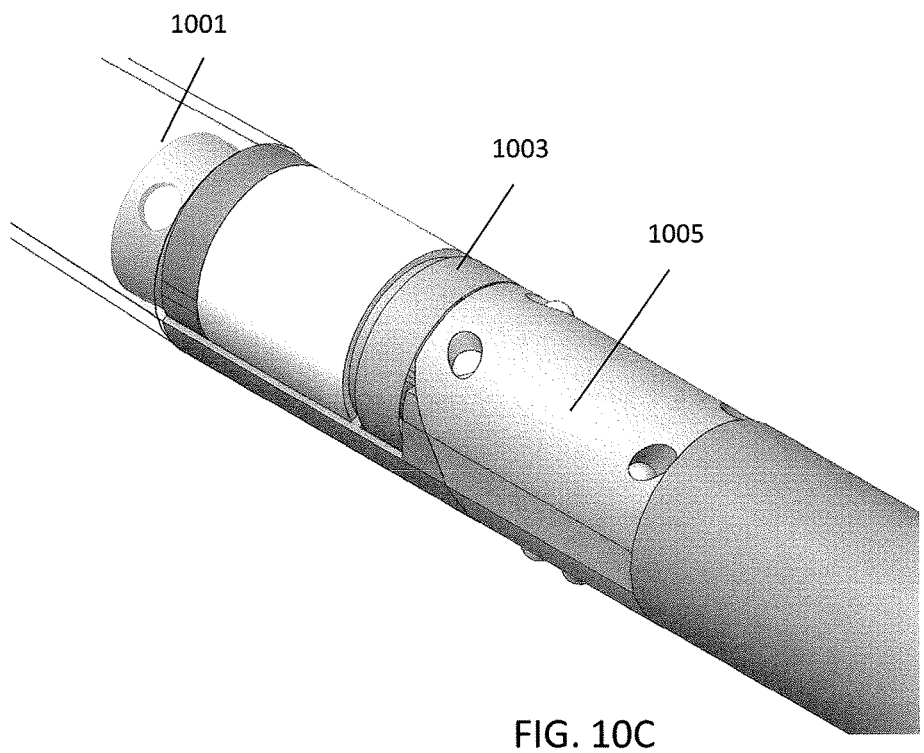
FIG. 10C is an enlarged perspective view of the junction between the annular cutting ring and rest of the catheter body of the device shown in FIG. 10A.
Figure 10D:
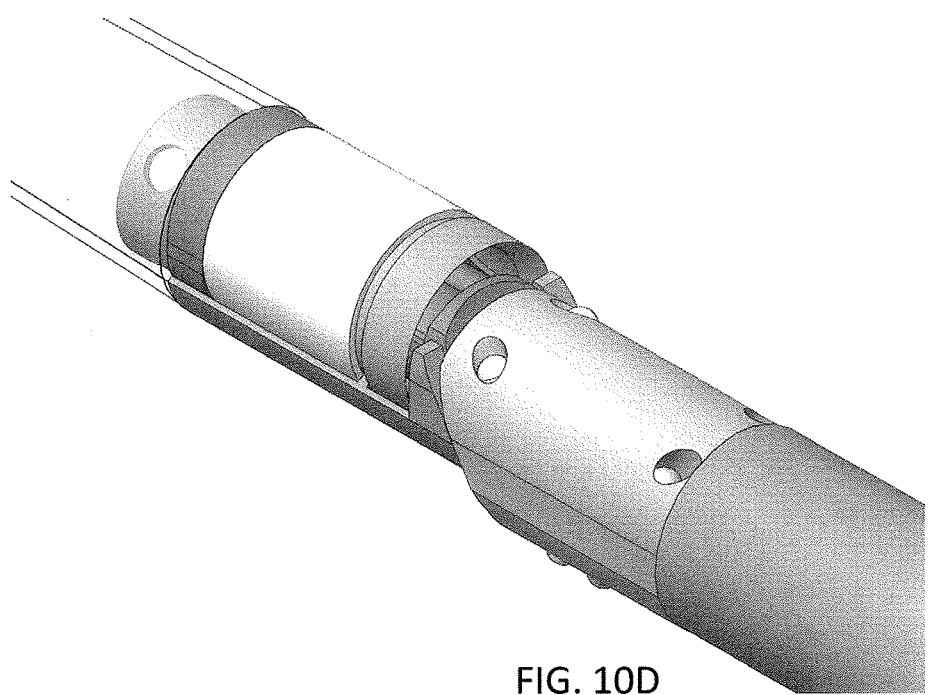
FIG. 10D is an enlarged perspective view of the junction between the annular cutting ring and rest of the catheter body of the device shown in FIG. 10B.

For example, FIGS. 10A and 10B show the distal region of the atherectomy catheter devices in both the non-activated and activated positions. In the closed/non-activated position shown in FIGS. 10A and 10C, the cutter 1003 is protected by the closed distal tip assembly 1001 and catheter body 1005 to prevent unintended damage to the inner diameter of ancillary medical devices and vasculature. In the open/activated position shown in FIGS. 10B and 10D, the tip assembly 1001 is raised to expose up to half of the cutter 1003 edge. When open, the top circumference of the cutter 1003 and distal tip assembly 1001 increases the overall crossing profile of the device. This maximum dimension between top of the cutter edge and the bottom of the catheter body extends the inner lumen of the artery and creates an opposing force for cutter engagement into the tissue. This appositional force will ensure the position of the cutting edge against the targeted cutting site will be enough to both engage the tissue and maintain contact during the cutting pass In the example shown in FIGS. 10A-10D, the annular cutting ring 1003 moves with the distal tip assembly 1001 when the distal tip assembly is laterally displaced. Further, the distal tip assembly includes a storage region 1205 (visible in FIGS. 12A-12B). Pulling the catheter after laterally displacing the cutter and distal tip region, e.g., in the direction indicated by the arrow 1010 in FIG. 10B, may result in tissue being cut and moved into the tissue storage region in the distal tip.

Figure 12A:
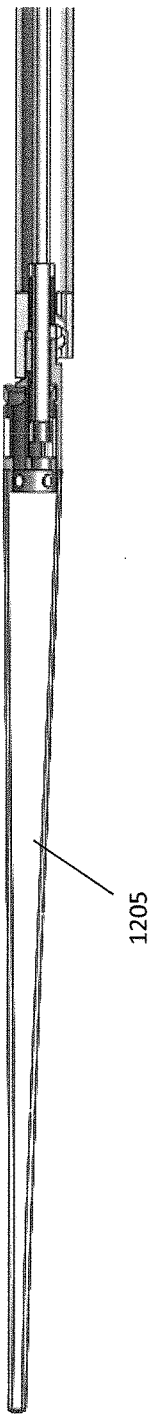
FIGS. 12A and 12B show cross-sectional views through a length of catheter such as the one shown in FIGS. 10A-10D.
Figure 12B:
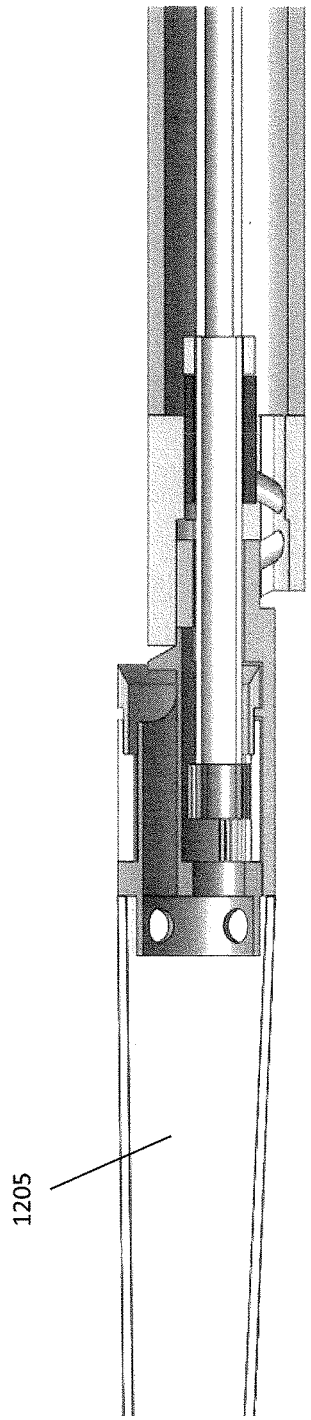

FIGS. 11A and 11B are an annotated illustration of the catheter shown in FIGS. 10A-10D. This example is also a gear-driven atherectomy catheter, and may also include a drive system such as the one illustrated above (e.g., FIGS. 4A-5). Thus, the device may include gear teeth on an inner surface of the annular cutting ring and a pinion gear driveshaft. FIGS. 12A and 12B show cross-sectional views through the variation of FIGS. 10A-10D. As mentioned, the distal tissue collection region 1205 is apparent.

This variation of the device may also include on-board and real time image guidance capabilities, as mentioned above, and may include an imaging element, or energy emitting assembly, to be positioned at the distal portion of the device such that local images of the vessel may guide device usage. The emitting element may be positioned distal and/or proximal to the cutter edge. Proximal placement would provide information during a cutting pass prior to the cutter interacting with the tissue and, therefore, allow the physician to stop or continue cutting as disease changes in depth and/or position. Distal placement would also provide guidance regarding cut quality, depth and cutting efficiency.

Furthermore, the data collected at the distal end of the catheter, after transmitted and appropriately processed, may drive an automated means of tip actuation and cutter position. Increased amounts of disease detected by the software may automatically increase tip axially offset consequently increasing cut depth and apposition force. Cutter speeds, gear ratios and torque inputs may be adjusted according to input from the imaging system.

Figure 13:
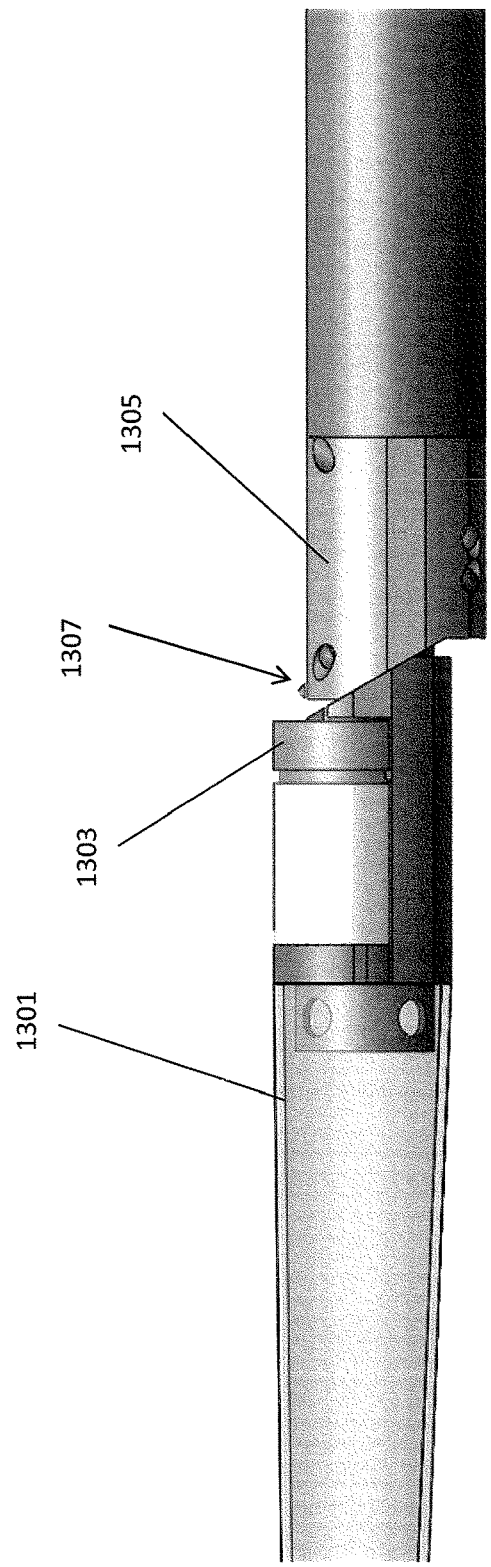
FIG. 13 shows an embodiment of an atherectomy catheter including an OCT imaging system.

For example, in FIG. 13, an OCT sensor/emitting element 1307 (which may correspond to the distal end of the optical fiber that forms part of the OCT system) is shown on the distal end of the catheter body 1305 device, immediately before the laterally displaceable annular cutting ring 1305 and distal tip assembly 1301. This may allow for visualization of the material before cutting when pulling the catheter to cut.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An atherectomy catheter device for cutting tissue in a vessel, the device comprising:
   an elongate, flexible catheter body having a proximal end and a distal end and a longitudinal axis;
   an elongate displaceable distal tip assembly;
   a rotatable annular cutting ring between the distal end of the catheter body and the distal tip assembly;
   a handle attached to the proximal end of the catheter, the handle including a control that is configured to expose a cutting edge of the annular cutting ring by displacing the distal tip assembly from a closed configuration in which the distal tip assembly is in-line with the catheter body to an open configuration in which the distal tip assembly is off-axis from the catheter body, wherein the rotatable annular cutting ring remains in-line with the distal end of the catheter body when the distal tip assembly is displaced and forms a distal cutting edge at the distal end of the catheter body;
   a balloon mounted on a circumference of the catheter body approximately 180 degrees from an exposed portion of the distal cutting edge, the balloon configured to inflate to urge the exposed portion of the distal cutting edge into the tissue; and
   an Optical Coherence Tomography (OCT) imaging subassembly comprising a fiber extending the length of the catheter body, a distal end of the fiber fixed in a position that is proximal to the distal cutting edge,
   wherein the OCT imaging subassembly is configured to be rotated to obtain angular survey images of the vessel.

2. The device of claim 1, further comprising a drive shaft extending along the length of the catheter body, wherein axial movement of the driveshaft moves the distal tip assembly between the open and closed configurations.

3. The device of claim 2, wherein the drive shaft comprises a cable drive shaft having a distal gear configured to drive rotation of the cutting ring.

4. The device of claim 2, wherein the drive shaft is directly connected to the annular cutting ring.

5. The device of claim 2, wherein the drive shaft comprises a hollow tubular drive shaft having a hollow lumen, the optical fiber extending within the hollow lumen.

6. The device of claim 1, wherein the annular cutting ring comprises internal gear teeth configured to mate with a drive shaft to rotate the cutting ring.

7. The device of claim 1, further comprising a guidewire lumen extending the length of the catheter.

8. The device of claim 1, wherein the annular cutting ring forms an outer surface of the catheter in both the closed and open configurations.

9. The device of claim 1, further comprising an internal tissue collection region configured to receive tissue cut by the annular cutting ring.

10. The device of claim 9, wherein the tissue collection region is located within the distal tip assembly.

11. The device of claim 9, wherein the tissue collection region is located within the catheter body.

12. An atherectomy catheter device for cutting tissue having a displaceable tip, the device comprising:
    an elongate catheter body having a longitudinal axis;
    a displaceable distal tip assembly attached to a distal end of the catheter body;
    an annular cutting ring between the catheter body and the distal tip assembly;
    an inflatable element near the distal end of the catheter body configured to displace the distal tip assembly relative to the elongate catheter body when inflated; and
    a handle attached to the elongate catheter body, the handle including a control that is configured to switch the distal tip assembly between a closed configuration, in which the distal tip assembly is in-line with the catheter body and the cutter is protected by the distal tip assembly, and an open configuration, in which the distal tip assembly is displaced from the catheter body, by inflating the inflatable element to move the distal tip assembly away from the distal end of the catheter body to expose a cutting edge of the annular cutting ring, wherein the annular cutting ring remains in-line with the distal end of the catheter body when the distal tip is displaced and forms an exposed distal cutting edge at the distal end of the catheter body, further wherein the inflatable element is positioned approximately 180 degrees from the exposed distal cutting edge when the distal tip is displaced.

13. The device of claim 12, further comprising a drive shaft extending along the length of the catheter body.

14. The device of claim 13, wherein the drive shaft comprises a cable drive shaft having a distal gear configured to drive rotation of the cutting ring.

15. The device of claim 13, wherein the drive shaft is directly connected to the annular cutting ring.

16. The device of claim 13, wherein the drive shaft comprises a hollow tubular drive shaft.

17. The device of claim 12, wherein the annular cutting ring comprises internal gear teeth configured to mate with a drive shaft to rotate the cutting ring.

18. The device of claim 12, further comprising a guidewire lumen extending the length of the catheter.

19. The device of claim 12, wherein the annular cutting ring forms an outer surface of the catheter in both the closed and open configurations.

20. The device of claim 12, further comprising an internal tissue collection region configured to receive tissue cut by the annular cutting ring.

21. The device of claim 20, wherein the tissue collection region is located within the distal tip assembly.

22. The device of claim 20, wherein the tissue collection region is located within the catheter body.

23. The device of claim 12, further comprising an OCT imaging subassembly.

24. The device of claim 23, wherein the OCT imaging subassembly comprises a fiber optic extending the length of the catheter body.

25. The device of claim 23, wherein the OCT imaging assembly comprises a side-facing OCT emitting element fixed proximal to the annular cutting ring.

26. The device of claim 23, wherein the OCT imaging assembly comprises a side-facing OCT emitting element fixed distally to the annular cutting ring.

* * * * *